Oct. 8, 1963 R. S. MOORE Plant Pat. 2,287
MINIATURE ROSE PLANT
Filed Aug. 22, 1962
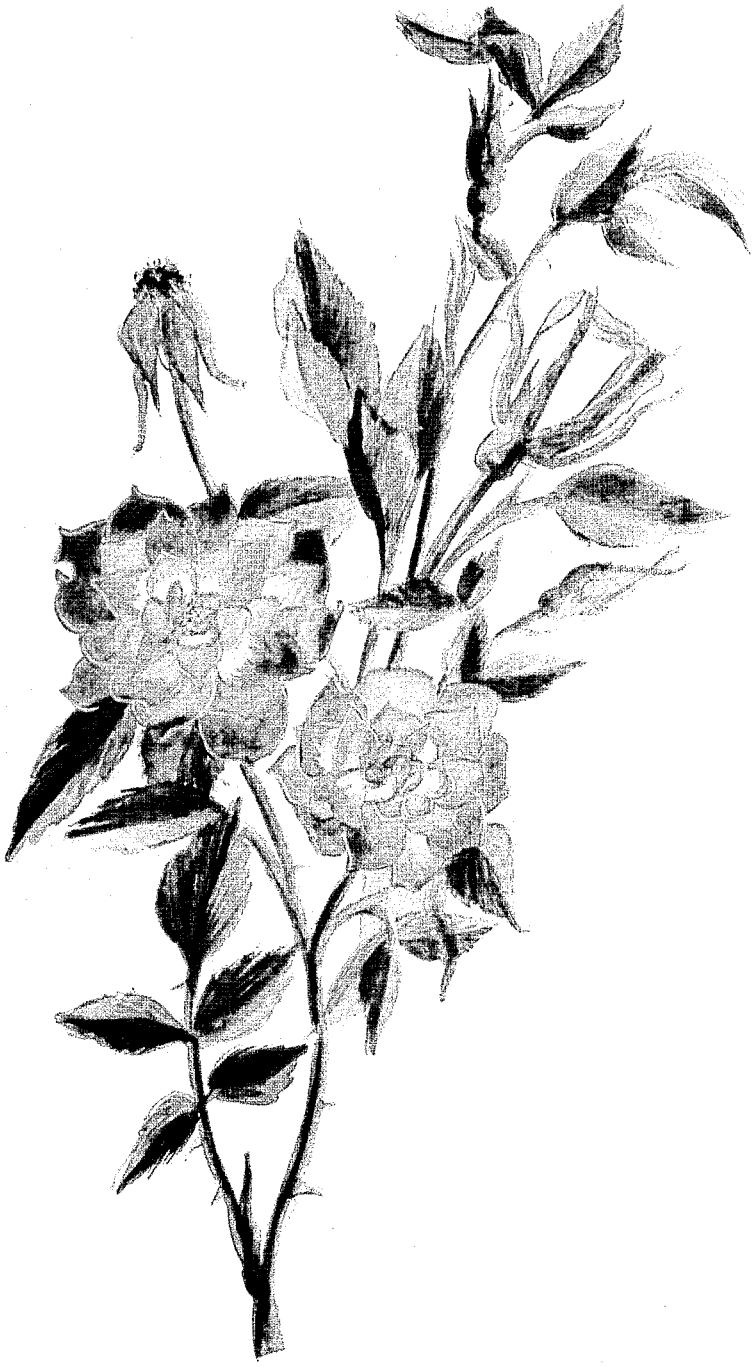
WITNESS
Jeanette Nunn Copley
INVENTOR
Ralph S. Moore
ATTORNEYS United States Patent Office Plant Pat. 2,287
Patented Oct. 8, 1963

2,287
MINIATURE ROSE PLANT

Ralph S. Moore, 2519 E. Mineral King, Visalia, Calif.

Filed Aug. 22, 1962, Ser. No. 218,797
1 Claim. (Cl. Plt.—7)

The present invention relates to a new and distinct variety of hardy, dwarf, bush type rose plant of the hybrid miniature class; the variety being primarily characterized—as to novelty—by brilliant bi-color flowers which, in general color effect, are bright red (or orange red), with yellow reverse.

Comparatively, the buds and opening flowers resemble the Talisman (unpatented) in form and color, but are in miniature and usually show more red.

The instant variety is further characterized by:

An abundance of bloom, with the flowers borne singly or several to stem in loose clusters.

A plant which is vigorous, rather upright, and with medium small foliage; the flowers and plant being somewhat larger than those of the average miniature rose, although with moderate pinching or trimming of the upright shoots the plant can be maintained low and bushy or spreading. The plant, which has a normal average height of 12" to 16" at maturity, is easily kept to a height of 12" by trimming the stronger growing canes to force side growth.

A plant which grows and blooms satisfactorily both in the greenhouse and outdoors; is a good potted plant; and provides excellent garden decoration, as well as cut flowers.

The present variety of miniature rose plant was originated by me in my nursery located at Visalia, California, under conditions of careful control and observation, as a cross between an unnamed and unpatented seedling (*Rosa wichuraiana* × Floradora, both unpatented) as the seed parent, and Little Showoff (United States Plant Patent No. 2,176) as the pollen parent.

Subsequent to origination of the variety I successfully asexually reproduced it, in my nursery located as aforesaid, by budding as well as cuttings; the reproductions having run true in all respects.

The FIGURE of the drawing illustrates a spray, including foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bush; seedling; greenhouse; outdoor; cut flowers; garden decoration; potted plant.

Class: Hybrid miniature.

Flowers:

*Continuity.*—Continuous.

*Fragrance.*—Moderate.

Flowers borne: Singly or several to stem in loose clusters on normal medium length stems.

Quantity of bloom: Abundant both outdoors and in greenhouse.

Bud:

*Peduncle.*—Medium length; slender; erect; medium green; smooth.

*Before calyx breaks.*—Size—small. Form—long; pointed; with foliaceous appendages on the surface of the bud; with much cut foliaceous parts extending beyond the tip of the bud equal to one-half of its length. Color—medium green.

*As calyx breaks.*—Color—Aureolin Yellow, 3, or Lemon Yellow, 4/1, at base, shading into Cadmium Orange, 8/2, and thence into Orpiment Orange, 10/2, on the upper two-thirds of the petal.

*As first petal opens*: Size—Small. Form—short; pointed. Color—Outside: Lemon Yellow, 4/1, at base, shading into Cadmium Orange, 8/2, thence into Orpiment Orange, 10/2; inside: Lemon Yellow, 4/1, at basal one-third, then into yellow overlaid with Cardinal Red, 822/2. Opening—normally opens well in any weather.

Bloom:

*Size when fully open.*—Small, averaging 1¼" to 1½".

*Petalage.*—Double, with from 35 to 75 petals, arranged regularly.

*Form.*—Cupped and full at first, becoming high centered; petals at first, and later at maturity, being loosely rolled outward.

Petals: Thin; soft; satiny, both inside and outside.

*Shape.*—Outside—broad lanceolate; intermediate—lanceolate; inside—lanceolate.

*Color.—Newly opened flower from plant grown outdoors (July 1962), Visalia, California*—Outside petal: outside surface—Lemon Yellow, 4/1, at base, shading into Cadmium Orange, 8/2, on upper two-thirds of petal; inside surface—Indian Yellow, 6/1, overlaid with Blood Red, 820/2 on upper two-thirds of petal. Intermediate petal: outside surface—Lemon Yellow, 4/1, at base, shading into Marigold Orange, 11/2; inside surface—Indian Yellow, 6/1, at base, shading into Currant Red, 821/2. Inner petal: outside surface—Lemon Yellow, 4/1, at base, shading into Marigold Orange, 11/2, and shaded or tinted red; inside surface—Indian Yellow, 6/1, at base, shading to Currant Red, 821. *A flower that was open for three days outdoors (July 1962), Visalia, California*—Outside petal: Outside surface—Indian Yellow, 6/2, at base, shading into Saturn Red, 13/3; inside surface—Indian Yellow, 6/2, at base, shading into Rose Madder, 23/1 or 23/2. Inside petal: Outside surface—Indian Yellow, 6/2, at base, shading into Saturn Red, 13/3; inside surface—Indian Yellow, 6/2, at base, shading into Rose Madder, 23/1.

*General color effect.*—Newly opened flower—bright orange-red, with yellow reverse. Three days open—as newly opened, but with more pink.

*Behavior.*—Drops off cleanly; early and late in the season, or during cooler weather the red color is usually darker. The yellow is most pronounced in warmer weather.

*Flower longevity (June 1962).*—Bush in garden—two to four days. Cut flowers kept at living room temperature—two to three days.

Reproductive organs:

*Stamens.*—Few; arranged regularly about pistils; mixed with petaloids.

*Filaments.*—Medium length; yellow; some without anthers.

*Anthers.*—Small; yellow; usually all open at once.

*Pollen.*—Sparse; lemon.

*Pistils.*—Medium number.

*Styles.*—Uneven; medium length; bunched.

*Stigma.*—White or pale yellow.

*Ovaries.*—All enclosed in calyx.

*Hips.*—Ovoid-globular; reddish; smooth; walls thin.

*Sepals.*—Permanent; long; spear shaped; recurved.

*Seeds.*—Few; small.

*Plant*

Foliage:

*Leaves.*—Compound of five leaflets; normal abundance; moderately small; moderately thin; semi-glossy.

*Leaflets.*—Shape: lanceolate. Apex: acute. Base: round. Margin: serrate. Color: medium to light green. Rachis: medium strength; upper side—almost smooth, grooved; under side—sparsely thorny. Stipules: medium length; narrow width; medium length points, turning out at an angle of about 45 degrees.

Growth:

*Habit.*—Dwarf; bushy; upright; much branched.

*Growth.*—Free; vigorous.

*Canes.*—Medium.

*Main stems.*—Color: green. Thorns: color—gray or gray-brown; several; medium length; straight or slightly hooked downward; short, oval base. Prickles: none. Hairs: none.

*Branches.*—Color: bright green. Thorns: several; medium length; straight; short, round base. Prickles: few. Hairs: none.

*New shoots.*—Color: bright green. Thorns: several; straight; short, round base. Prickles: none. Hairs: none.

The miniature rose plant and its flowers as herein described may vary in slight detail due to climatic and soil conditions under which the variety may be grown; the present description being of the variety as grown at Visalia, California.

The following is claimed:

A new and distinct variety of miniature rose plant of hardy, dwarf, upright, much branched, bush type, as illustrated and described, characterized by buds and opening flowers resembling the Talisman in form and color but in miniature and usually showing more red; the flowers being bi-color and in general color effect being a brilliant red to orange-red, with yellow reverse; and further characterized by a plant which is vigorous in growth, with medium small foliage and an abundance of bloom, with the flowers borne singly or several to stem in loose clusters.

No references cited.